United States Patent [19]

Berg et al.

[11] Patent Number: 5,173,156

[45] Date of Patent: Dec. 22, 1992

[54] DEHYDRATION OF FORMIC ACID BY EXTRACTIVE DISTILLATION

[75] Inventors: Lloyd Berg, 1314 S. 3rd Ave., Bozeman, Mont. 59715; Kraig M. Wendt; Rudolph J. Szabados, both of Bozeman, Mont.

[73] Assignee: Lloyd Berg, Bozeman, Mont.

[21] Appl. No.: 803,509

[22] Filed: Dec. 9, 1991

[51] Int. Cl.$^5$ .................. B01D 3/40; C07C 53/02
[52] U.S. Cl. .................................... 203/15; 203/51; 203/56; 203/57; 203/60; 203/61; 203/62; 203/63; 203/65; 562/609
[58] Field of Search ............... 203/15, 16, 56, 62, 203/51, 60, 61, 57, 63, 65; 562/609, 608

[56] References Cited

U.S. PATENT DOCUMENTS

| 2,526,508 | 10/1950 | Scheeline et al. | 203/15 |
| 2,588,268 | 3/1952 | Mercer et al. | 203/15 |
| 3,040,094 | 6/1962 | Stine et al. | 203/15 |
| 3,394,058 | 7/1968 | Hohenschutz | 203/62 |
| 4,353,784 | 10/1982 | Koga et al. | 203/16 |
| 4,729,818 | 3/1988 | Berg | 203/62 |
| 4,735,690 | 4/1988 | Berg et al. | 203/62 |
| 4,786,370 | 11/1988 | Berg | 203/51 |

Primary Examiner—Wilbur Bascomb, Jr.

[57] ABSTRACT

Formic acid cannot be completely removed from formic acid—water mixtures by distillation because of the presence of the maximum azeotrope. Formic acid can be readily removed from mixtures containing it and water by using extractive distillation in which the extractive distillation agent is cyclohexanone, isophorone or a mixture of these with certain organic compounds. Typical examples of effective agents are cyclohexanone; isophorone; cyclohexanone and neodecanoic acid; isophorone and diisobutyl ketone.

3 Claims, No Drawings

DEHYDRATION OF FORMIC ACID BY EXTRACTIVE DISTILLATION

This application is related to application Ser. No. 07/591,249, now abandoned.

FIELD OF THE INVENTION

This invention relates to a method for dehydrating formic acid using certain higher boiling liquids as the agent in extractive distillation.

DESCRIPTION OF PRIOR ART

Extractive distillation is the method of separating close boiling compounds or azeotropes by carrying out the distillation in a multiplate rectification column in the presence of an added liquid or liquid mixture, said liquid(s) having a boiling point higher than the compounds being separated. The extractive agent is introduced near the top of the column and flows downward until it reaches the stillpot or reboiler. Its presence on each plate of the rectification column alters the relative volatility of the close boiling compouds in a direction to make the separation on each plate greater and thus require either fewer plates to effect the same separation or make possible a greater degree of separation with the same number of plates. When the compounds to be separated normally form an azeotrope, the proper agents will cause them to boil separately during the extractive distillation and thus make possible a separation in a rectification column that cannot be done at all when no agent is present. The extractive agent should boil higher than any of the close boiling liquids being separated and not form minimum azeotropes with them. Usually the extractive agent is introduced a few plates from the top of the column to insure that none of the extractive agent is carried over with lowest boiling component. This usually requires that the extractive agent boil twenty Centigrade degrees or more than the lowest boiling component.

At the bottom of a continuous column, the less volatile components of the close boiling mixtures and the extrcative agent are continuously removed from the column. The usual methods of separation of these two components are the use of another rectification column, cooling and phase separation or solvent extraction.

There are currently two commercial methods for manufacturing formic acid. One is the reaction of caustic soda with carbon monoxide under pressure to produce sodium formate. This is then hydrolysed with sulfuric acid to yield the formic acid. The other is to obtain the formic acid as a by-product from the oxidation of n-butane. Both of these processes yield an aqueous mixture of formic acid. However the components of this mixture cannot be separated by conventional rectification because formic acid boils at 100.8° C., only 0.8° C. above water and because these two form a maximum azeotrope boiling at 107.2° C. and containing 22.5 wt. % water. Thus it is impossible to separate completely formic acid from water by rectification because of the closeness of the boiling points and because as soon as the maximum azeotrope composition is attained, no further change in composition will occur.

Extractive distillation would be an attractive method of effecting the separation of formic acid from water if agents can be found that (1) will break the formic acid-water azeotrope and (2) are easy to recover from formic acid, that is, form no azeotrope with formic acid and boil sufficiently above formic acid to make the separation by rectification possible with only a few theoretical plates.

Extractive distillation typically requires the addition of an equal amount to twice as much extractive agent as the formic acid-water on each plate of the rectification column. The extractive agent should be heated to about the same temperature as the plate into which it is introduced. Thus extractive distillation imposes an additional heat requirement on the column as well as somewhat larger plates. However this is less than the increase occasioned by the additional agents required if the separation is done by azeotropic distillation. Another consideration in the selection of the extractive distillation agent is its recovery from the bottoms product. The usual method is by rectification in another column. In order to keep the cost of this operation to a minimum, an appreciable boilng point difference between the compound being separated and the extractive agent is desirable. It is desirable that the extractive agent be miscible with formic acid otherwise it will form a two-phase azeotrope with the formic acid in the recovery column and some other method of separation will have to be employed.

Recent developments in separating formic acid from water by extractive distillation have been reported. Kokai, Japanese Patent 82-24,324, Feb. 8, 1982 used amines and phosphate esters as the agents. Cohen, U.S. Pat. No. 4,576,683 describes the use of lactams and Berg, U.S. Pat. No. 4,642,166 employed sulfolanes as the agents in this separation.

OBJECTIVE OF THE INVENTION

The object of this invention is to provide a process or method of extractive distillation that will enhance the relative volatility of water from formic acid in their separation in a rectification column. It is a further object of this invention to identify suitable extractive distillation agents which will eliminate the formic acid-water azeotrope and make possible the production of pure formic acid and water by rectification. It is a further object of this invention to identify organic compounds which in addition to the above constraints, are stable, can be separated from formic acid by rectification with relatively few theoretical plates and can be recycled to the extractive distillation column and reused with little decomposition.

SUMMARY OF THE INVENTION

The objects of the invention are provided by a process for separating formic acid from water which entails the use of cyclohexanone or isophorone, either alone or admixed with certain oxygenated organic compounds.

DETAILED DESCRIPTION OF THE INVENTION

We have discovered that cyclohexanone or isophorone, either alone of admixed with other organic compounds, will effectively negate the formic acid-water maximum azeotrope and permit the separation of pure water from formic acid by rectification when employed as the agent in extractive distillation. Table 1 lists cyclohexanone and its mixtures and the approximate proportions that have found to be effective. Table 2 lists isophorone and its mixtures that are effective. The data in Tables 1 and 2 were obtained in a vapor-liquid equilibrium still. In each case, the starting material was the formic acid-water azeotrope. The ratios are the parts by weight of extractive agent used per part of formic acid-water azeotrope. The relative volatilities are listed for starting material is the formic acid-water azeotrope which possesses a relative volatility of 1.00.

TABLE 1

Extractive Distillation Agents Containing Cylcohexanone

| Compounds | Ratios | | Relative Volatilities |
|---|---|---|---|
| Cyclohexanone | 1 | 6/5 | 2.0 2.6 |
| Cyclohexanone, Dipropylene glycol dibenzoate | $(1/2)^2$ | $(3/5)^2$ | 2.1 2.0 |
| Cyclohexanone, Decanoic acid | " | " | 1.9 2.0 |
| Cyclohexanone, Heptanoic acid | " | " | 3.1 3.5 |
| Cyclohexanone, Hexanoic acid | " | " | 1.8 2.2 |
| Cyclohexanone, Neodecanoic acid | " | " | 1.7 2.3 |
| Cyclohexanone, Octanoic acid | " | " | 1.8 2.2 |
| Cyclohexanone, Octanoic - Decanoic acids | " | " | 1.8 1.8 |
| Cyclohexanone, Pelargonic acid | " | " | 1.8 2.4 |
| Cyclohexanone, Decanoic acid, Dipropylene glycol dibenzoate | $(1/3)^3$ | $(2/5)^3$ | 2.4 2.8 |
| Cyclohexanone, Decanoic acid, Heptanoic acid | " | " | 1.7 1.7 |
| Cyclohexanone, Decanoic acid, Hexanoic acid | " | " | 1.6 1.7 |
| Cyclohexanone, Decanoic acid, Octanoic acid | " | " | 2.1 3.1 |
| Cyclohexanone, Decanoic acid, Octanoic - Decanoic acids | " | " | 1.5 1.9 |
| Cyclohexanone, Decanoic acid, Pelargonic acid | " | " | 2.1 2.4 |
| Cyclohexanone, Heptanoic acid, Dipropylene glycol dibenzoate | " | " | 1.7 1.8 |
| Cyclohexanone, Heptanoic acid, Hexanoic acid | " | " | 2.4 3.0 |
| Cyclohexanone, Heptanoic acid, Neodecanoic acid | " | " | 1.9 1.8 |
| Cyclohexanone, Heptanoic acid, Octanoic - Decanoic acids | " | " | 1.6 1.9 |
| Cyclohexanone, Heptanoic acid, Diethylene glycol dibenzoate | " | " | 1.7 1.8 | each of the two ratios employed. The compounds which are effective when used in mixtures with cyclohexanone are hexanoic acid, heptanoic acid, octanoic acid, pelargonic acid, decanoic acid, neodecanoic acid and dipropylene glycol dibenzoate. The compounds which are effective when used in mixtures with isophorone are hexanoic acid, heptanoic acid, octanoic acid, pelargonic acid, decanoic acid, neodecanoic acid, acetyl salicyclic acid, diisobutyl ketone, diethylene glycol dibenzoate, dipropylene glycol dibenzoate, acetophenone, 2-hydroxyacetophenone, methyl salicylate, methyl phenyl acetate, 4-hydroxyacetophenone, 2-nitrotoluene and 3-nitrotoluene. The two relative volatilities shown in Tables 1 and 2 correspond to the two different ratios investigated. For example, in Table 1, one part of cyclohexanone with one part of the formic acid-water azeotrope give a relative voltatility of 2.0, 6/5 parts of cyclohexanone give 2.6. One half part of cyclohexanone mixed with one half part of heptanoic acid with one part of the formic acid-water azeotrope gives a relative volatility of 3.1, 3/5 parts of cyclohexanone plus 3/5 parts of heptanoic acid gives 3.5. From Table 2, one third part of isophorone plus ⅓ part of decanoic acid plus ⅓ part of acetophenone with one part of the formic acid-water azeotrope gives a relative volatility of 2.5, with 2/5 parts, these three give a relative volatility of 2.7. In every example in Tables 1 and 2, the One of the compounds, isophorone, listed in Table 2 and whose relative volatility had been determined in the vapor-liquid equilibrium still, was then evaluated in a glass perforated plate rectification column possessing 4.5 theoretical plates and the results listed in Table 3. The data in Table 3 was obtained in the following manner. The charge was 85 wt. % formic acid and 15% water and after a half hour of operation in the 4.5 theoretical plate column to establish equilibrium, isophorone at 95° C. and 20 ml/min. was pumped in. The rectification was continued with sampling of overhead and bottoms after one hour. The analysis is shown in Table 3 and was 87.6% water, 12.4% formic acid in the overhead and 24% water, 76% formic acid in the bottoms which gives a relative volatility of 2.0 of water to formic acid. After 1.5 hours of total operating time, the overhead analysed 89% water, 11% formic acid and the bottoms was 23% water, 77% formic acid which is a relative volatility of 2.15. This indicates that the maximum azeotrope has been negated and separation accomplished. Without the extractive agent, the overhead would have approached the maximum azeotrope composition which is 22.5% water. This proves that the extractive agent is negating the azeotrope and makes the rectification proceed as if the azeotrope no longer existed and brings the more volatile component, water, out as overhead. And this from formic acid which normally boils only 0.8° C. higher.

TABLE 2

Extractive Distillation Agents Containing Isophorone

| Compounds | Ratios | | Relative Volatilities |
|---|---|---|---|
| Isophorone | 1 | 6/5 | 2.0 2.3 |
| Isophorone, Diisobutyl ketone | $(1/2)^2$ | $(3/5)^2$ | 1.6 1.7 |
| Isophorone, Dipropylene glycol dibenzoate | " | " | 2.0 2.9 |
| Isophorone, 2-Hydroxyacetophenone | " | " | 1.8 2.2 |
| Isophorone, Methyl phenyl acetate | " | " | 2.0 1.9 |
| Isophorone, Decanoic acid | " | " | 2.1 2.7 |
| Isophorone, Heptanoic acid | " | " | 2.0 2.6 |
| Isophorone, Hexanoic acid | " | " | 1.9 2.5 |
| Isophorone, Neodecanoic acid | " | " | 1.8 2.5 |
| Isophorone, Octanoic acid | " | " | 2.7 3.0 |
| Isophorone, Octanoic - Decanoic acids | " | " | 2.5 2.4 |

TABLE 2-continued
Extractive Distillation Agents Containing Isophorone

| Compounds | Ratios | | Relative Volatilities |
|---|---|---|---|
| Isophorone, Pelargonic acid | " | " | 2.2 2.4 |
| Isophorone, Hexanoic acid, Diisobutyl ketone | (1/3)[3] | (2/5)[3] | 1.7 2.0 |
| Isophorone, Hexanoic acid, Diethylene glycol dibenzoate | " | " | 2.4 2.5 |
| Isophorone, Hexanoic acid, Dipropylene glycol dibenzoate | " | " | 2.8 1.9 |
| Isophorone, Hexanoic acid, Neodecanoic acid | " | " | 2.1 2.6 |
| Isophorone, Hexanoic acid, 2-Hydroxyacetophenone | " | " | 1.8 1.7 |
| Isophorone, Hexanoic acid, 4-Hydroxyacetophenone | " | " | 2.1 2.4 |
| Isophorone, Hexanoic acid, Methyl phenyl acetate | " | " | 1.8 2.4 |
| Isophorone, Heptanoic acid, Diisobutyl ketone | " | " | 1.6 1.3 |
| Isophorone, Heptanoic acid, Diethylene glycol dibenzoate | " | " | 2.0 3.0 |
| Isophorone, Heptanoic acid, Dipropylene glycol dibenzoate | " | " | 2.4 2.4 |
| Isophorone, Heptanoic acid, Octanoic - Decanoic acids | " | " | 2.3 2.9 |
| Isophorone, Heptanoic acid, Pelargonic acid | " | " | 1.7 2.3 |
| Isophorone, Heptanoic acid, 2-Hydroxyacetophenone | " | " | 2.1 2.3 |
| Isophorone, Heptanoic acid, Methyl salicylate | " | " | 1.6 1.8 |
| Isophorone, Heptanoic acid, 3-Nitrotoluene | " | " | 1.7 1.8 |
| Isophorone, Octanoic acid, Neodecanoic acid | " | " | 1.7 2.1 |
| Isophorone, Octanoic acid, Diethylene glycol dibenzoate | " | " | 3.2 3.5 |
| Isophorone, Octanoic - Decanoic acids, Nitrobenzene | " | " | 1.6 1.7 |
| Isophorone, Octanoic - Decanoic acids, Dipropylene glycol dibenzoate | " | " | 1.9 2.3 |
| Isophorone, Pelargonic acid, Acetophenone | " | " | 2.4 2.5 |
| Isophorone, Pelargonic acid, Diethylene glycol dibenzoate | " | " | 2.0 2.2 |
| Isophorone, Pelargonic acid, Dipropylene glycol dibenzoate | " | " | 2.1 2.1 |
| Isophorone, Pelargonic acid, Octanoic - Decanoic acids | " | " | 2.5 2.5 |
| Isophorone, Pelargonic acid, 2-Octanone | " | " | 2.3 2.4 |
| Isophorone, Pelargonic acid, Decanoic acid | " | " | 2.0 2.6 |
| Isophorone, Pelargonic acid, Methyl phenyl acetate | " | " | 1.8 2.4 |
| Isophorone, Pelargonic acid, 2-Nitrotoluene | " | " | 2.2 2.4 |
| Isophorone, Pelargonic acid, 3-Nitrotoluene | " | " | 2.0 2.3 |
| Isophorone, Decanoic acid, Acetophenone | " | " | 2.5 2.7 |
| Isophorone, Acetyl salicylic acid, Diisobutyl ketone | " | " | 1.6 1.6 |
| Isophorone, Acetyl salicylic acid, Anisole | " | " | 1.8 1.9 |

TABLE 3
Data From Run Made In Rectification Column With Isophorone

| | Wt. % - 1 hr. | Wt. % - 1.5 hrs. |
|---|---|---|
| Overhead - Water | 87.6 | 89 |
| Formic Acid | 12.4 | 11 |
| Bottoms - Water | 24 | 23 |
| Formic Acid | 76 | 77 |
| Relative Volatility | 2.0 | 2.15 |

THE USEFULNESS OF THE INVENTION

The usefulness or utility of this invention can be demonstrated by referring to the data presented in Tables 1, 2 and 3. All of the successful extractive distillation agents show that formic acid and water can be separated from their maximum azeotrope by means of distillation in a rectification column and that the ease of separation as measured by relative volatility is considerable. Without these extractive distillation agents, no improvement above the azeotrope composition will occur in the rectification column. The data also show that the most attractive agents will operate at a boilup rate low enough to make this a useful and efficient method of recovering high purity formic acid from any mixture with water including the maximum azeotrope. The stability of the compounds used and the boiling point difference is such that complete recovery and recycle is obtainable by a simple distillation and the amount required for make-up is small.

WORKING EXAMPLES

EXAMPLE 1

Fifty grams of the formic acid-water azeotrope and fifty grams of isophorone were charged to an Othmer type glass vapor-liquid equilibrium still and refluxed for 12 hours. Analysis of the vapor and liquid by gas chromatography gave vapor composition of 64.8% water, 35.2% formic acid; liquid composition of 47.7% water, 52.3% formic acid. This indicates a relative volatility of 2.0. Ten grams of isophorone were added and refluxing continued for another eleven hours. Analysis indicated a vapor composition of 64.6% water, 35.4% formic acid; a liquid composition of 44% water, 56% formic acid which is a relative volatility of 2.3.

EXAMPLE 2

Fifty grams of the formic acid-water azeotrope, 25 grams of cyclohexanone and 25 grams of heptanoic acid were charged to the vapor-liquid equilibrium still and refluxed for eleven hours. Analysis indicated a vapor composition of 47.9% water, 52.1% formic acid; a liquid composition of 36.4% water, 63.6% formic acid which is a relative volatility of 3.1. Five grams of cyclohexanone and five grams of heptanoic acid were added and refluxing continued for another eleven hours. Analysis indicated a vapor composition of 64.1% water, 35.9% formic acid; a liquid composition of 34% water, 66% formic acid which is a relative volatility of 3.5.

EXAMPLE 3

Fifty grams of the formic acid-water azeotrope, 17 grams of isophorone, 17 grams of decanoic acid and 17 grams of acetophenone were charged to the vapor-liquid equilibrium still and refluxed for 16 hours. Analysis indicated a vapor composition of 64.7% water, 35.3% formic acid; a liquid composition of 42.3% water, 57.7% formic acid which is a relative volatility of 2.5. Three grams each of isophorone, decanoic acid and acetophenone were added and refluxing continued for another eleven hours. Analysis indicated a vapor composition of 65.2% water, 34.8% formic acid; a liquid composition of 41.4% water, 58.6% formic acid which is a relative volatility of 2.7.

EXAMPLE 4

A glass perforated plate rectification column was calibrated with ethylbenzene and p-xylene which possesses a relative volatility of 1.06 and found to have 4.5 theoretical plates. A solution comprising 340 grams of formic acid and 60 grams of water was placed in the stillpot and heated. When refluxing began, an extractive agent consisting of pure isophorone was pumped into the column at a rate of 20 ml/min. The temperature of the extractive agent as it entered the column was 95° C. After establishing the feed rate of the extractive agent, the heat input to the formic acid and water in the stillpot was adjusted to give a total reflux rate of 10-20 ml/min. After one hour of operation, the overhead and bottoms samples of approximately two ml. were collected and analysed using gas chromatography. The overhead analysis was 87.6% water, 12.4% formic acid. The bottoms analysis was 24% water, 76% formic acid. Using these compositions in the Fenske equation, with the number of theoretical plates in the column being 4.5, gave an average relative volatility of 2.0 for each theoretical plate. After 1½ hours of total operating time, the overhead and bottoms samples were again taken and analysed. The overhead composition was 89% water, 11% formic acid and the bottoms composition was 23% water, 77% formic acid. This gave an average relative volatility of 2.15 for each theoretical plate.

We claim:

1. A method for recovering formic acid from a mixture consisting solely of formic acid and water which comprises distilling said mixture of formic acid and water in a rectification column in the presence of about one part of an extractive agent per part of said formic acid-water mixture, recovering water as overhead product and obtaining the formic acid and the extractive agent from the stillpot, wherein the extractive agent consists of cyclohexanone.

2. A method for recovering formic acid from a mixture consisting solely of formic acid and water which comprises distilling said mixture of formic acid and water in a rectification column in the presence of about one part of an extractive agent per part of said formic acid-water mixture, recovering water as overhead product and obtaining the formic acid and the extractive agent from the stillpot, wherein the extractive agent consists of isophorone.

3. A method for recovering formic acid from a mixture consisting solely of formic acid and water which compriese distilling said mixture of formic acid and water in a rectification column in the presence of about one part of an extractive agent per part of said formic acid-water mixture, recovering the water as overhead product and obtaining the formic acid and the extractive agent from the stillpot, wherein the extractive agent comprises isophorone and at least one material selected from the group consisting of, diisobutyl ketone, 4-hydroxyacetophenone, methyl phenyl acetate, 2-nitrotoluene, 2-octanone and anisole.

* * * * *